United States Patent [19]

Sampson

[11] Patent Number: 5,092,849
[45] Date of Patent: Mar. 3, 1992

[54] IMPLANTABLE DEVICE

[75] Inventor: Edward J. Sampson, Carlisle, Mass.

[73] Assignee: Shiley Infusaid, Inc., Norwood, Mass.

[21] Appl. No.: 469,895

[22] Filed: Jan. 24, 1990

Related U.S. Application Data

[63] Continuation-in-part of Ser. No. 242,445, Sep. 9, 1988, abandoned, which is a continuation-in-part of Ser. No. 89,113, Aug. 25, 1987, abandoned.

[51] Int. Cl.$^5$ .............................................. A61M 5/32
[52] U.S. Cl. .................................... 604/175; 604/93; 604/283
[58] Field of Search ................... 604/175, 93, 86, 283

[56] References Cited

U.S. PATENT DOCUMENTS 3,310,051  4/1967  Schulte .
4,781,695  11/1988  Dalton ................................. 604/93
4,886,501  12/1989  Johnson et al. .................... 604/175
4,915,690  4/1990  Cone et al. ...................... 604/175 X

FOREIGN PATENT DOCUMENTS 0233986  8/1986  European Pat. Off. .
0230747  12/1986  European Pat. Off. .
8701041  2/1987  PCT Int'l Appl. .

Primary Examiner—John D. Yasko
Attorney, Agent, or Firm—Sughrue, Mion, Zinn Macpeak & Seas

[57] ABSTRACT

A device that is implantable to provide access to multiple body sites for the administration or withdrawal of fluids. A hollow port has a self sealing septum on one end and an outlet at an opposite end. A catheter is connected to the outlet. The septum and outlet are positioned to be substantially in-line.

20 Claims, 4 Drawing Sheets

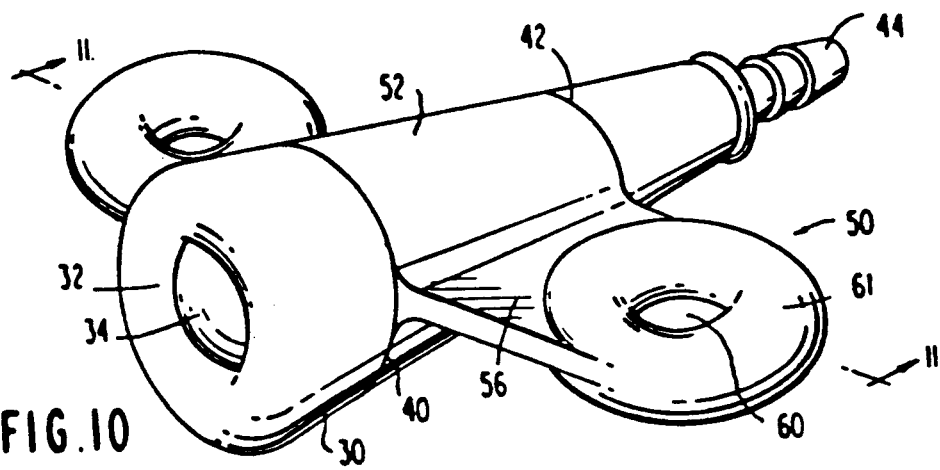
FIG.10
FIG.11
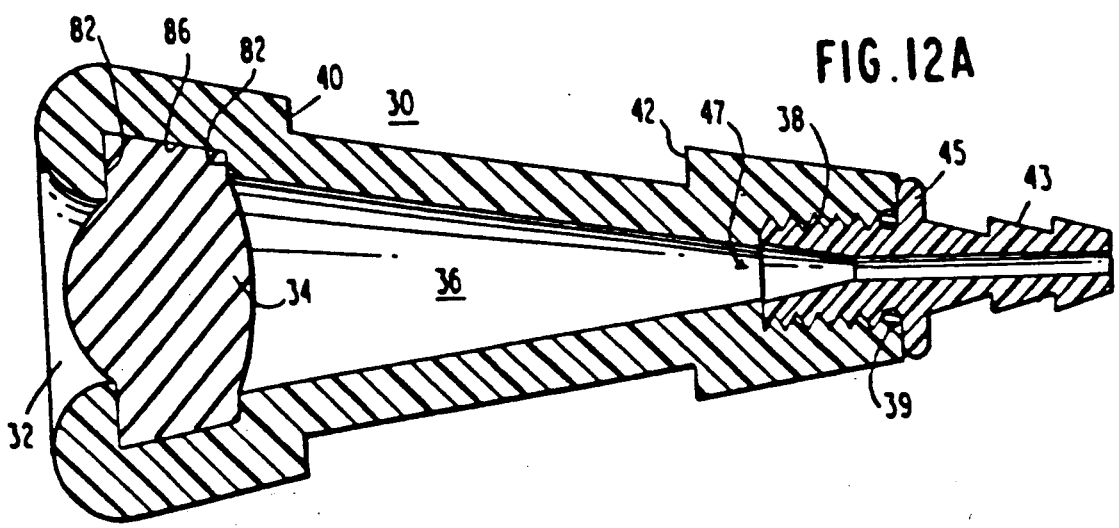
FIG.12A
FIG.12B

IMPLANTABLE DEVICE

This application is a continuation-in-part of application Ser. No. 07/242,445, filed Sept. 9, 1988, now abandoned which was a continuation-in-part of application Ser. No. 07/89,113, filed Aug. 25, 1987, now abandoned.

BACKGROUND OF THE INVENTION

This invention relates to an implantable device and in particular, to a vascular access device that is implanted subcutaneously.

Within the prior art, a variety of implantable access devices are known. Typical is the commercially available INFUSAID Infuse-A-Port TM. These techniques of providing access via an implantable device include percutaneous catheters, implantable ports having access to a port at a perpendicular angle to the skin and direct access with a needle. Thus, in the case of the commercially available Infuse-A-Port TM, a base having an inlet located under the skin having an access outlet perpendicular to the skin line. The catheter thus extends at a right angle to the direction of needle access to the port's inlet.

Materials which are used in these devices generally include various plastics such as teflon, polyethylene, polypropylene, polyurethane, polycarbonate, polyethersulfone, polysulfone, polyolefin, nylon and the like. Additionally, silicone rubber, stainless steel and titanium are used.

A hallmark characteristic of all previous techniques of access utilizing implantable ports is a requirement that a needle be placed into the port septum at a 90° angle to the outlet catheter. This is acceptable for bolus injections or infusions over brief periods of time. However, for longer infusions or for continuous infusions with these ports, a right angle needle is required to allow for the hub of the needle to be parallel with the skin. This is required to permit anchoring of the needle to the body throughout the time of infusion.

Another disadvantage with such prior art devices is that they require a minor but distinct surgical procedure for implantation. That is, the size of the base is such that a significant incision is required for implantation. Moreover, given the size of the base, implantation is restricted specific portions of the body, for example, the chest and stomach area that can physically support and house the port without protuberances or discomfort to the patient.

Given these deficiencies of prior art devices, it is an object of this invention to define an implantable access device for humans, the device having a low profile capable of implantation in a variety of bodily locations, which provides access to multiple body sites.

Yet another object of this invention is to define a low, acute angle implantable port which provides access to multiple body sites for research purposes in animals.

Yet another object of this invention is to provide an acute angle implantable device providing access to multiple body sites in small patients, such as infants, neonates and children.

A further object of this device is to provide for an implantable port which has a reduced size such that implantation can be carried out minimizing both the surgical procedure time and size of the incision.

These and other objects of this invention are achieved by means of an acute angle port having a port body holding a self sealing septum. The port body has grooves, wings, or flaps which allow for suturing the port to subcutaneous tissue. The self sealing septum in accordance with this invention has the ability to be connected to various catheters such that when coupled, the port provides direct facile access to the catheter. This direct access to the catheter allows for catheter tip placement or for the management of blockages in the catheter. Such is extremely difficult in the context of ports which are disposed at right angles to the catheter connection.

These and other objects of this invention are set forth herein by reference to the attached drawings and the descriptions of the preferred embodiments which follows.

BRIEF DESCRIPTION OF THE DRAWINGS

FIG. 10 is a perspective view of a second embodiment of a molded tie-down element;

FIG. 11 is a cut-away view of FIG. 10; and

FIGS. 12A and 12B illustrate a sixth embodiment of this invention.

DESCRIPTION OF THE PREFERRED EMBODIMENTS

Figure 1:
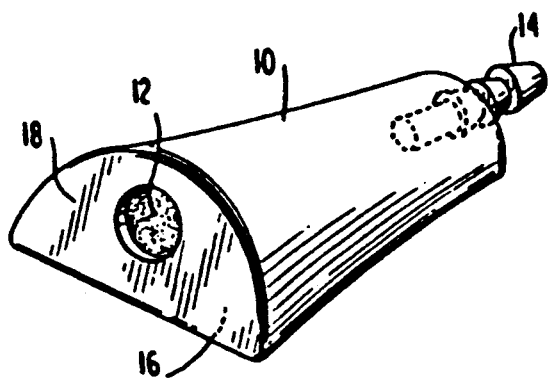
FIG. 1 is a schematic perspective view of a first embodiment of an implantable port in accordance with this invention.

Referring now to FIG. 1, a first embodiment of the implantable port of this invention is illustrated. The port comprises a body member 10 having a self sealing septum 12 and an outlet connecter 14 to which a suitable catheter is mounted. As illustrated in FIG. 1, the port has a generally flat base area 16 with an inclined face 18 into which the septum is placed. The septum provides a small diameter target, typically 0.15–0.20 inches. The overall length of the device from the front face to the tip of the connecter is in the range of one inch. The overall height of the device from the flat base 16 to the tapered top portion is at a maximum approximately 0.38 inches. The port and the connecter is manufactured from a biocompatible material. Materials of choice for the port are silicone rubber and various plastics such as teflon, polyethylene, polypropylene, polyurethane, polycarbonate, polyethersulfone, polysulfone, polyolefin, nylon, and the like. The connecter is preferably a metallic member made of stainless steel or titanium. The entire body and connector can be made of one piece from any suitable metal or plastic.

As illustrated in FIG. 1, the front face 18 is inclined so that access to the self sealing septum 12 is axially aligned with the connecter 14. This is in contrast to prior art systems wherein normal access to the septum would be disposed at a right angle, that is perpendicular to the outlet connecter to the catheter.

Given the low profile of the device, implantation in areas with limited subcutaneous tissue such as forearms, scalp and neck area, infants and children and their appendages is possible.

Figure 2:
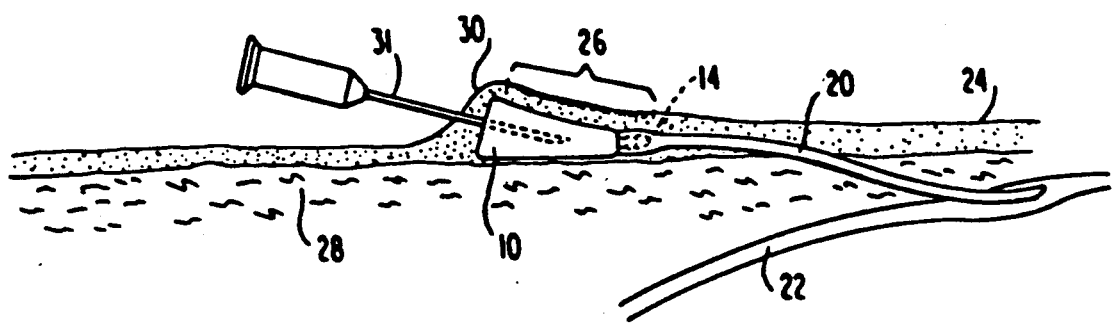
FIG. 2 is a schematic illustration showing the placement of the implantable port of this invention subcutaneously with the catheter extended into a blood vessel.

Referring now to FIG. 2, the device of FIG. 1, including the catheter, is shown implanted. Specifically, the port 10 has coupled to it a catheter 20 of suitable length. The catheter is force-fitted onto the connecter 14 having its free end lanced into a suitable blood vessel 22. The catheter made from a biocompatible material such as silicone rubber or polyurethane and depending on the application may have a radiopaque material added. The device is implanted under the skin 24 by making a small localized incision 26. The incision is shallow and does not involve incursion into underlying muscle tissue 28. Given the low profile of the device, a small protrusion 30 in the skin is present but such is not obtrusive or acts in any way as an impediment to normal functioning at the implantation site.

Access to the device 10 is by means of a needle 31. As can be seen from FIG. 2, the needle penetrates the skin at the protrusion 30 directly into the target or port zone 12 and is in line with the outlet 14. A major advantage of this system is that given the in-line nature of the septum, outlet and catheter access to the catheter tip for management of blockages is possible. This also allows the use of straight needles as illustrated in FIG. 2 for access to the port since entry is generally parallel to the skin line. Moreover, if it is necessary to pass a guide wire through the port and into the catheter, such can be done without making any significant bends. The ability to pass a guide wire or other appropriate device into the catheter after implantation provides a significant advantage in terms of clearing the catheter or importantly, initially placing the catheter tip at an appropriate location within the body. Such is extremely difficult in prior art right angle systems.

As can be appreciated from FIG. 2, the use of a straight needle provides a material advantage over prior techniques. Additionally, if the needle is required to be taped down then, it is a simple matter of affixing the needle when in contact with the septum to the skin yet not substantially immobilize the patient. Thus, for example, if the port 10 is implanted in an arm the needle can simply be taped or strapped in place thereby anchoring the needle to the body during infusion or injections requiring a long period of time.

Figure 3:
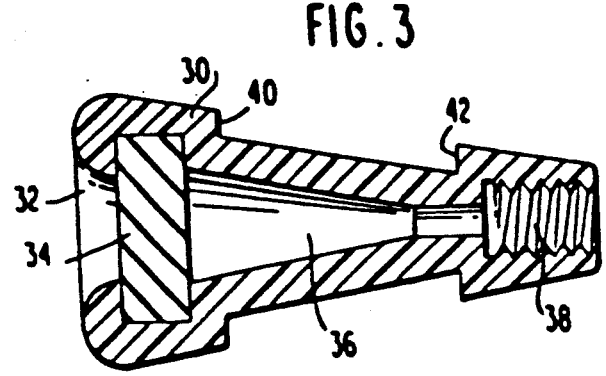
FIG. 3 is a schematic cut-away view of a second embodiment of this invention.
Figure 9:
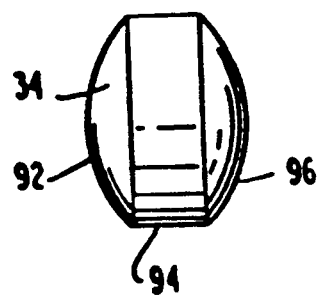
FIG. 9 illustrates a septum shaped prior to installation in the FIG. 8 device.

FIG. 3 illustrates a second embodiment of an in-line port in accordance with this invention. As illustrated in FIG. 3, the port is generally conical and comprises the body member 30 having an opening 32. A self sealing septum 34 is placed into the body 30 to close off the opening 32 and provide a suitable target. In this embodiment, the septum is a circular disk bulging only slightly when installed. The shape is illustrated in FIG. 9. The port has a hollow portion 36 generally axially in line with the self sealing septum 34. The hollow portion serving as a reservoir terminates into a zone which is tapped, that is, area 38 to allow for the catheter connection. The overall length of the device is in the range of 0.75-1.0 inches. The maximum diameter is in the range of 0.4 inches. The exposed area, that is, opening 32 is in the range of 0.25 inches. As in the case of the first embodiment a variety of materials may be used, such as polysulfone.

The device of FIG. 3 has two annular shoulders 40 and 42. These shoulders provide zones for holding a tie-down element (not illustrated) around the device.

Figure 4:
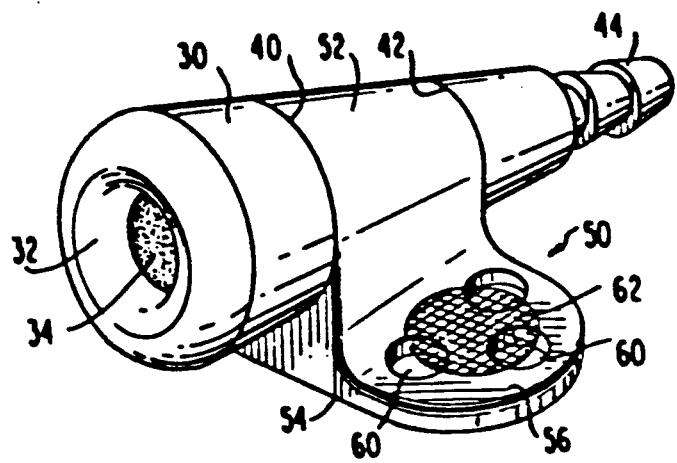
FIG. 4 is a perspective view of the embodiment of FIG. 3 utilizing a separately molded tie-down element.
Figure 5:
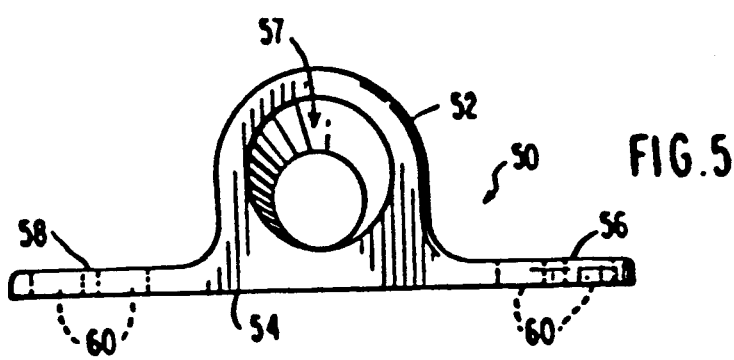
FIG. 5 is an end view of the tie-down element of FIG. 4.

Referring now to FIGS. 4 and 5, a perspective view of the port illustrated in FIG. 3 is depicted. The numerals used to identify the same aspects of the embodiment of FIG. 3 are used in FIGS. 4 and 5. Additionally, FIG. 4 illustrates the connecter 44 for the catheter coupled to the outlet portion of the port, that is, screwed into the zone 38 and having a series of annular barbs or serrations upon which the catheter is fixed.

As illustrated in FIG. 5 the tie-down comprises a separate element which is of a separately molded material. Specifically, the tie-down 50 comprises a body portion 52 inclined to the horizontal relative to a base portion 54. Through an opening 57, the device 30 is inserted such that as illustrated in FIG. 4 the rear portion of the device at shoulder 42 abuts against the rear portion of the tie-down while the front portion rests against shoulder 40. Consequently, when snapped into position the tie-down inclines the port and provides a pair of extending "wings" for purposes of suturing the device into place. Various techniques of suturing the wings 56, 58 may be used. As illustrated in FIG. 4, a series of holes 60 can allow for sutures to be stitched through and around each of the wings. Alternatively, a zone of exposed dacron fabric 62 may be used to provide a confined anchoring area on each of the wing surfaces.

FIGS. 10 and 11 illustrate a second preferred embodiment of the tie-down of this invention. FIG. 11 is a cut-away view along line 11—11 in FIG. 10. To the extent that common elements involved the same numbers are used as in the case of FIGS. 4 and 5.

The tie-down 50 of this preferred embodiment comprises a circular body portion 52 into which the device 30 is inserted. As in the case of FIG. 4, the shoulders 40 and 42 define limits of an annular portion of the body 30 having decreased thickness to lock the tie-down 50 in place. Thus, when snapped into position in FIGS. 10 and 11, the tie-down is disposed axially symmetrically with the body 30 as illustrated in FIG. 11. A pair of extending wings 56 and 58 are employed for purposes of suturing.

In the embodiment of FIGS. 10 and 11 each of the wings has a circular doughnut shaped portion 61 of increased thickness having a through-hole 60. The increased thickness of the doughnut 61 provides the necessary structural support for the sutures without tearing the material. Alternatively, to save space the tie-down of FIG. 10 can be further modified so that only a portion of the doughnut immediately adjacent to the wings 56-58 is employed with the sutures then looping through the web portion of the wing 56, 58 and around only the area of increased thickness immediately adjacent thereto. As is apparent from the embodiment of FIGS. 10 and 11, with the use of the tie-down a smooth tapered surface is formed on the exterior of the port body 30.

Figure 6:
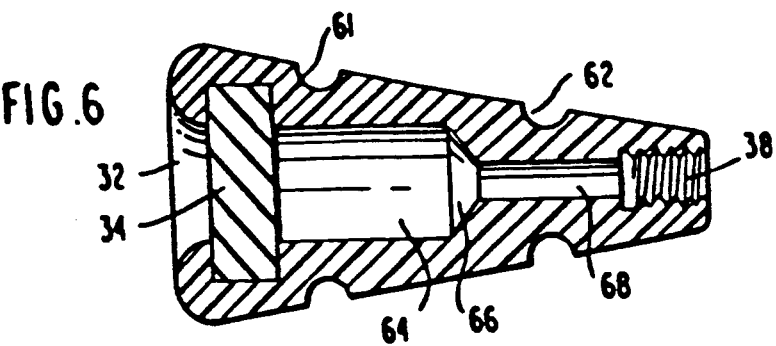
FIG. 6 is a schematic cut-away view of a third embodiment of this invention.

Referring now to FIG. 6, a third preferred embodiment of this invention is illustrated. The embodiment of FIG. 6 departs from that illustrated in FIG. 3 in that the device while retaining its generally truncated conical form eliminates the shoulder zones 40 and 42. In its place two annular rings 61 and 62 are employed. These provide two suture hold down locations. Another variation is that the hollow area 64 in the embodiment of FIG. 6 is generally cylindrical and has a truncated zone 66 coupling a straight in-line portion 68 to the hollow area 64. This serves as a guide for the needle, it being understood that the needle would generally terminate in the zone 64 providing direct fluid access to the catheter through the barbed connector which would be screwed into the device at the threaded portion 38.

Figure 7:
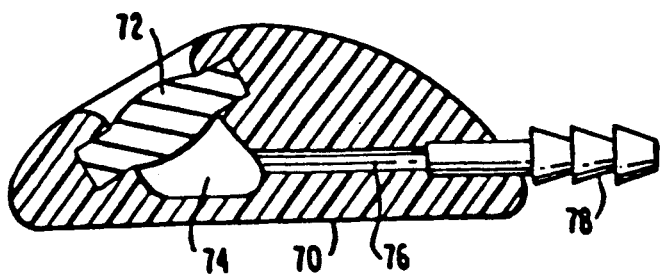
FIG. 7 is a schematic cut-away side view of a fourth embodiment of this invention.

Referring now to FIG. 7, a fourth embodiment of this invention is depicted. In FIG. 7, the device comprises a generally squat body portion 70 having a self sealing septum 72 embedded therein. The septum 72 is inclined relative to the horizontal flat bottom portion of the device and has a cavity portion 74 defined within the body 70. An outlet hollow port 76 is in fluid communication with an external connecter piece 78. The connecter piece is force-fitted or the like into the body portion 70 and serves as the connector between the port and the catheter. The body portion may be made of polysulfone or the like and, as illustrated in FIG. 7 has a very low profile. Needle access is provided at a normal angle to the self sealing septum 72 resulting in a shallow acute angle between needle and skin surface. The device is anchored in place by through-holes, wings or the like which are not illustrated.

Figure 8:
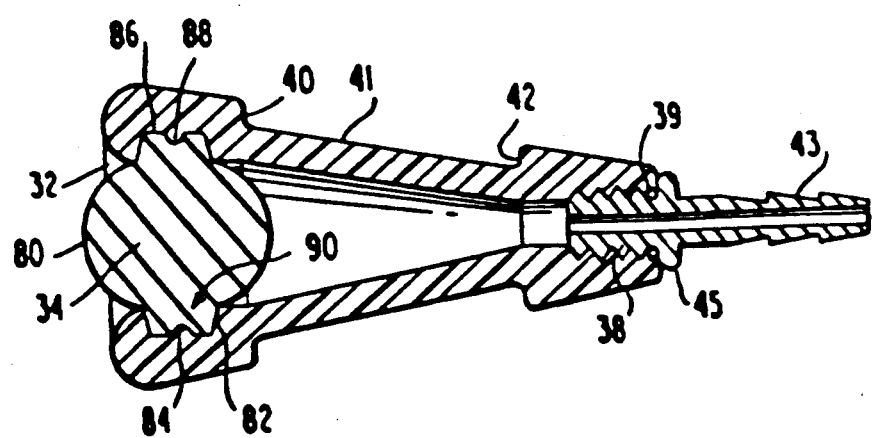
FIG. 8 is a schematic cut-away side view of a fifth embodiment of this invention.

Referring to FIGS. 8 and 9, a fifth embodiment of this invention is depicted. This embodiment is generally similar to that of FIG. 3 with the exception that the self-sealing septum has been modified. To the extent that common numerals are used in describing the port body as in FIG. 3, such have been used in FIG. 8. Thus, the port is generally conical and comprises a body having an opening 32. A pair of annular shoulders 40 and 42 provides a zone for holding a tie-down element around the device in the recess 41 such as the wing tie-down as illustrated in FIG. 4 and FIG. 10. If necessary an O-ring seal 39 may be used with the connection 43 which extends beyond the body. That catheter connection may also have a shoulder 45 which defines a positive stop limiting insertion of the catheter connection into the port body.

In accordance with this embodiment of the invention, the self-sealing septum 34 prior to assembly comprises a generally cylindrical shape having the dome-shaped surfaces 92 and 96 as illustrated in FIG. 9. Faces 82 in the port body further define an annular recess 86. The opening 32 of the port comprises compatible structure to lock the septum into place. Thus, as illustrated in FIG. 8, the port comprises an annular recess 86 which engages the annular surface 94 on the septum. The recess 86 has an annular protrusion 88 which forms the annular recess 84 around the septum. This defines a positive seal zone 90 around the septum.

This embodiment offers improvements over the septum of FIGS. 3 or 6 in that the increased depth of the septum, given its spherical shape, provides increased needle holding force to resist pull out and provide necessary lateral rigidity. Additionally, the septum is easier to install due to its own rounded shape and because of the open recess in the port body formed by faces 82.

The septum is inserted and deforms from the shape of FIG. 9 so that its annular surface 94 fully engages the recess 86 in the body thereby defining a positive lock in recess 86 and a high pressure seal ridge is impressed in the septum by the annular protrusion 88. This seal in the form of groove 84 is formed because the septum is made preferably of a soft silicone rubber while the annular protrusion 88 is made of a harder material. Given that material the striking face deforms outward upon insertion to a curvature illustrated in FIG. 8 as 80 from the shape 92 in FIG. 9.

Referring now to FIGS. 12A and 12B a sixth preferred embodiment of this invention is depicted. The numerals used in FIGS. 12A and 12B conform to those previously to the extent that they identify common elements.

The embodiment of FIGS. 12A and 12B employs a modified septum 34 and a modified catheter fitting 43. As illustrated in FIG. 12A, the port body 30 has an opening 32 into which the septum 34 is mounted. A hollow cavity 36 defines the interior of the port. The external body has a pair of shoulders 40 and 42 to serve as stops for a tie-down, as illustrated in FIG. 10. The outlet 38 is threaded and has, if necessary, an o-ring seal 39. A stop 45 in the form of a shoulder defines a positive physical limit for insertion of the catheter connection 43. As illustrated in FIG. 12A the catheter connection 43 also has a series of barbs 45 to hold and secure a catheter in place.

In accordance with the embodiment of FIG. 12A, the cavity 36 has a continuous taper which is matched by the taper 47 on the inlet of the catheter connection. This interior geometry thus defines a unitary taper from the septum 34 into the catheter connection 43. This is ideal for using guide wire technology where a guide wire can be introduced through the septum and fed through the port catheter to reestablish patency in the case of system clogging.

The embodiment of FIG. 12 also utilizes a modified septum. As illustrated in FIG. 12B this septum is a truncated conical section having convex faces 92 and 94. FIG. 12B illustrates the septum prior to insertion into the body of FIG. 12A. FIG. 12A illustrates the septum 34 deformed in its inserted condition. Faces 82 in the port body define an annular recess 86. Thus, as illustrated in FIG. 12A when the septum 34 is installed it will engage the recesses 86 defining a positive seal zone around the septum. Because the septum is made from a material which is softer than that of the body, the septum being typically made of soft silicone rubber, a deformation will occur so that a domed shaped striking surface is formed as illustrated in FIG. 12A.

This embodiment offers improvements in that it is easier to install into the body and provides better holding force for the needle together with better puncture life.

It is apparent that while multiple embodiments of this invention have been illustrated, various other modifications can be made without departing from the essential scope of the invention. A key aspect is the geometry of the device so that straight needles can be used with the device implanted at a very shallow implantation site within an arm, the neck area or the like. Such is considered a material advantage over prior art systems which must be implanted in the torso given their overall size and geometry.

Having described my invention I claim:

1. A body implantable access device comprising; a cylindrical hollow port, said port having an inlet, an internal cavity and an outlet, a self sealing septum subcutaneously disposed in and covering said inlet, said septum having a shaped target face and positioned in said port at substantially a right angle to said outlet such that a needle puncturing a skin line and said target face of said septum will be substantially in line with said outlet.

2. The implantable device of claim 1 further comprising means to mount a catheter at said outlet and a flexible catheter mounted on said means to mount a catheter to provide fluid access to a portion of the body in which said device is implanted.

3. The implantable device of claim 2 wherein said means to mount a catheter comprises a hollow connector one end of which is inserted into said outlet of said port, said hollow connector having an internal wall aligned with a wall of said internal cavity.

4. The implantable device of claim 1 further comprising means to anchor said port subcutaneously at an angle substantially parallel with the skin line at the implantation site.

5. The implantable device of claim 4 wherein said means to anchor comprises first and second shoulder portions provided on said port, said shoulder portions extending circumferentially around said port.

6. The implantable device of claim 4, wherein said means to anchor comprises a tie-down member attached to said body, said tie-down member having extending surfaces defining a suture area.

7. The implantable device of claim 4 wherein said means to anchor comprises a tie-down member having means to mount to said body, said tie-down member further including a flat portion defining a suture area.

8. The implantable device of claim 1 wherein said self sealing septum comprises a generally spherically shaped body having an annular surface, said annular surface engaging said hollow port.

9. The implantable device of claim 8 wherein said port further comprises an annular recess having an annular protrusion and defining said inlet, said septum deformable in said annular surface by said annular protrusion to lock and seal said septum in place in said opening.

10. The implantable device of claim 1, wherein said self-sealing septum comprises a generally cylindrical body having a convex front and rear face.

11. A body implantable device providing access to an internal portion of a living body for the administration and withdrawal of fluids comprising:
a hollow port made of a biocompatible material, said port having wall portions defining an inlet and an outlet, axially aligned with each other, a self-sealing septum member subcutaneously positioned in and covering said inlet, said port having an infusion chamber upstream of said outlet and blocked from the inlet by said self sealing septum, and said self sealing septum oriented in said inlet at substantially a right angle to said outlet such that a needle passing through skin and said septum will stop in said infusion chamber and will be substantially in line with said outlet.

12. The implantable device of claim 11 further comprising means to mount a catheter at said outlet and a flexible catheter mounted on said means to mount a catheter to provide fluid access to a portion of the body in which said device is implanted.

13. The implantable device of claim 12 wherein said means to mount a catheter comprises a hollow connector one end of which is inserted into said outlet of said port and the other end having annular barbs engaging said catheter.

14. The implantable device of claim 11 further comprising means to anchor said port subcutaneously at an angle substantially parallel with the skin line at the implantation site.

15. The implantable device of claim 14 wherein said means to anchor comprises first and second shoulder portions provided on said port, said shoulder portions extending circumferentially around said port.

16. The implantable device of claim 11 wherein said self sealing septum member comprises a member having a convex striking face and an annular flat surface, said annular flat surface engaging said port body for locking and sealing said septum into place.

17. The implantable device of claim 16 wherein said port body inlet comprises an annular recess having an annular protrusion, said self sealing septum member having an annular flat surface, said annular protrusion engaging and deforming said annular flat surface to lock said self sealing septum member into position in said port body.

18. The implantable device of claim 11, wherein said self-sealing septum member comprises a generally cylindrical member having a convex striking face.

19. The implantable device of claim 11, wherein said self-sealing septum member comprises a conical member having a convex striking surface.

20. The implantable device of claim 19, wherein said infusion chamber has a conical interior wall.

* * * * *